United States Patent [19]

De Vries

[11] Patent Number: 4,797,468

[45] Date of Patent: Jan. 10, 1989

[54] PREPARATION OF POLYLACTIC ACID AND COPOLYMERS OF LACTIC ACIDS

[75] Inventor: Klaas S. De Vries, Dieren, Netherlands

[73] Assignee: Akzo N.V., Arnhem, Netherlands

[21] Appl. No.: 130,905

[22] Filed: Dec. 10, 1987

[30] Foreign Application Priority Data

Dec. 19, 1986 [NL] Netherlands ................. 8603231

[51] Int. Cl.$^4$ ................. C08G 63/08; C07D 319/12
[52] U.S. Cl. ................. 528/354; 549/274
[58] Field of Search ................. 528/354; 549/274

[56] References Cited

U.S. PATENT DOCUMENTS

| | | | |
|---|---|---|---|
| 3,435,008 | 3/1969 | Schmitt et al. | 549/274 X |
| 3,457,280 | 7/1969 | Schmitt et al. | 528/354 X |
| 3,597,449 | 8/1971 | DeProspero et al. | 549/274 |
| 4,650,851 | 3/1987 | Rhum et al. | 528/354 |
| 4,727,163 | 2/1988 | Bellis | 549/274 |

*Primary Examiner*—Earl Nielsen
*Attorney, Agent, or Firm*—William M. Blackstone

[57] ABSTRACT

The invention relates to a method for preparing high molecular polylactic acid or copolymers of lactic acids using lactide that is purified by extraction with water.

10 Claims, No Drawings

PREPARATION OF POLYLACTIC ACID AND COPOLYMERS OF LACTIC ACIDS

The invention relates to a method for preparing polylactic acid or copolymers of lactic acid, in particular copolymers of lactic acid and glycolic acid.

Polylactic acid can be obtained by polycondensation of lactic acid, a polymer with a relatively low molecular weight being obtained with the elimination of water. Similarly, a copolymer having low molecular weight is obtained on condensing a mixture of lactic acid and glycolic acid. In most cases these polymers are not usable for many applications, and in particular, are not usable for application as a biodegradable polymer.

Polylactic acid having a higher molecular weight can be virtually exclusively obtained by decomposing the above-mentioned low-molecular polylactic acid by thermal treatment, a stable compound consisting of two lactic acid radicals according to the formula:

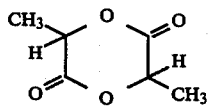

being obtained. A high-molecular polylactic acid can be obtained by polymerizing this compound (I), termed lactide, provided this starting compound does not contain any impurities which interfere with the progress of the polymerization.

The literature therefore recommends recrystallizing this starting substance at least once and, preferably, several times.

Such a recrystallization results, however, in considerable lactide losses. If the lactide has been prepared by thermal decomposition of a polylactic acid obtained by polycondensation of L-lactic acid or of D-lactic acid, the losses still remain limited to the normal losses virtually unavoidable in recrystallization.

However, the losses become more dramatic if a lactide has been prepared by thermal decomposition of a polylactic acid obtained by polycondensation of D,L-lactic acid (rac-lactic) acid. The reason is that this thermal decomposition produces a lactide which consists of a mixture of DL-lactide, LL-lactide and DD-lactide. For a random chain degradation 50%, 25% and 25% would be expected respectively; as a result of steric effects and/or racemization however, these values turn out to be somewhat different in practice, and a ratio of approximately 40% DL-, 30% LL- and 30% DD-lactide is usually found. It now appears that the solubility of the DL-lactide is many times greater than the solubility of the mixture of LL-lactide and DD-lactide. DL-lactide does not crystallize out if the two other isomers are present. Hence, about half of the lactide available for the polymerization is therefore lost on recrystallizing the lactide (mixture) from D,L-lactic acid.

A method has now been found for preparing high-molecular polylactic acid of polymers in which the yield of lactide available for the polymerization, and therefore of the final polymer, is considerably increased and in many cases is even doubled.

It is one object of the invention to provide a method for preparing polylactic acid or copolymers of lactic acid by polymerizing the lactide according to formula I, optionally in the presence of other poly- or monomers, the said lactide I being obtained by polycondensation of L-, D-, or D,L-lactic acid followed by decomposition of the low-molecular polylactic acid thus obtained, characterized in that the crude lactide is dissolved in an organic solvent which is liquid under the given conditions and which is not miscible with water, and this solution is then extracted with water in which a basic substance is dissolved which is not soluble, or only very sparingly soluble in the said organic solvent, after which the lactide is isolated from the organic solvent layer and (optionally after further purification) is used for polymerization or copolymerization to a high-molecular polylactic acid or copolymer thereof.

Surprisingly, said extraction method according to the invention removes precisely those impurities occurring in the crude lactide according to formula I which apparently influence the course of the polymerization and in one way or another affect the chain length without large losses being produced in relation to the lactide usable and available for the polymerization.

A second object of the invention is to provide a method for the preparation of a lactide of formula I by polycondensation of L-, D- or D,L-lactic acid followed by decomposition of the low-molecular polylactic acid thus obtained, characterised in that the crude lactide thus obtained is dissolved in an organic solvent, which is not miscible or virtually not miscible with water, and this solution is then extracted with water, in which a basic substance is dissolved which is not soluble or only sparingly soluble in said organic solvent, after which the lactide is isolated from the organic solvent layer.

In principle, it is possible to use as organic solvent all organic compounds which, under the given reaction conditions, are able to form a liquid phase which is not miscible with water and in which the crude lactide according to formula I is soluble. Preferably, organic solvents are chosen which do not dissolve water at all or dissolve water only to a very limited extent.

In addition, for practical reasons preference is given to organic liquids which have a boiling point between approximately 35° C. and 150° C. under atmospheric conditions and whose density differs from that of the aqueous phase to such an extent that a good phase separation is possible on the basis of the difference in density.

Organic solvents which are preferably suitable for use in the present invention are dichloro and trichloro methane, alkyl acetates such as ethyl-, propyl- and n-butyl acetate, ethers such as diethyl ether, ketones such as methyl ethyl ketone and methyl isobutyl ketone and aromatic hydrocarbons such as toluene and o- m- or p-xylene.

Excellently suitable are the solvents dichloromethane and ethyl acetate.

As basic substances to be dissolved in the aqueous phase, all those bases are in principle suitable which are insoluble, or only very sparingly soluble, in the organic solvent described above. In general, preference is given to water-soluble hydroxides, carbonates and hydrogen carbonates of alkaline metals and alkaline earth metals such as sodium hydroxide, sodium carbonate, sodium hydrogen carbonate, barium hydroxide and calcium hydroxide.

Weakly basic buffer solutions of, for example, sodium hydrogen carbonate or of disodium hydrogen phosphate can also be used satisfactorily.

The quantity of the basic substance in the water phase is not critical, but very good results are obtained if the number of base equivalents in the water phase is roughly equal to 2 to approximately 6 times the quantity of base which is necessary to titrate the same quantity of crude lactide with the base sodium isopropanolate (0.1 molar solution of sodium isopropanolate in isopropanol) until the colour changes according to the procedure specified in more detail under "titration".

The temperature at which the extraction according to the invention is carried out is not critical either, but the temperature must not, of course, be so high that the crude lactide dissolved in the organic liquid decomposes (or hydrolyses). Excellent results are obtained at room temperature but lower or higher temperatures are also quite possible.

A further improvement in the purity of the lactide can also be obtained by dissolving an inert salt, for example sodium chloride or sodium sulphate, to a high concentration in the aqueous phase. Good results are obtained by first shaking or stirring the lactide solution with an almost saturated solution of the salt in water and repeating this after adding (a solution of) the basic substance.

The lactide purified by the extraction method according to the invention is then polymerized in the usual manner (optionally in the presence of another monomer or polymer) to form the desired high-molecular poly-lactic acid or copolymer of polylactic acid.

In particular, the high-molecular polylactic acid and the copolymer with glycolic acid, which are obtained from a lactide consisting of a mixture of DD-, LL- and a significant percentage of DL-lactide, exhibit clear structural differences from the high-molecular polylactic acid or copolymer obtained after recrystallizing the crude lactide mixture. This difference in structure is ascribed to the proportionately larger number of pairs of two consecutive lactic acid units which have the LD or DL sequence. These differences in structure can be detected by simple physical-chemical methods, for example $^{13}C$ nmr.

The high-molecular polylactic acid, and in particular the copolymers of lactic acid and glycolic acid, are preferably used in pharmacy and medicine as biodegradable polymers. Thus, threads of polylactic acid or copolymers thereof find application as surgical sewing threads. In pharmacy, polylactic acid and copolymers of lactic acid and glycolic acid are used in particular as carriers for the controlled release of medicines. By way of example reference is made in this connection to the U.S. Pat. No. 3,773,919 (Boswell).

Titration

1–3 g of lactide is accurately weighed out to 0.01 g and dissolved in 25–50 ml of acetone dried over molecular sieve. After adding a few drops of a solution of bromothymol blue in acetone (60 mg in 20 ml) titration is carried out with a 0.1 M solution of sodium isopropanolate in isopropanol until the colour changes to blue and remains blue or bluish green for at least 30 sec. The consumption in mmol of isopropanolate per kg of lactide is hereinafter termed "base consumption" and expressed in milliequivalents per kg of lactide.

The "base consumption" determined in this manner serves as a measure of the quantity of basic substance which is used in the aqueous phase when using the extraction method according to the invention.

EXAMPLE 1

1. Lactide from rac-lactic acid

A mixture of 3,295 g of 90% rac-lactic acid and 16.4 g of zinc powder was heated to approximately 200° C. while stirring and distilling off water. Then the pressure was gradually reduced to approximately 5 mbar with continuous heating. After a leading fraction had first been collected, 1,621 g of lactide was collected as the main fraction. On titration as described above, the base consumption of the lactide thus prepared was 380 meq per kg of lactide.

2. Composition of the lactide

The lactide was analysed by gas chromatography. For this purpose a packed column having a length of 1.7 m was used. The packing consisted of 4% OV 225 on Chromosorb W-AW-DMCS, 80–100 mesh, and the column temperature was 140° C. Two main peaks were found in the chromatogram of unpurified lactide made from rac-lactic acid, retention times 255 and 362 sec. respectively. Making use, inter alia, of the results of the mass spectrometry analysis, it is assumed that the first peak represents the trans-lactide (DL-lactide) and the second peak represents the cis-lactide (DD and/or LL). Approximately 40:60 is always found for the mutual ratio of the integrated signals. It is assumed that this ratio also represents the weight ratio because it is probable that these two compounds, which are very similar to each other, will give virtually the same signal per unit of weight in the flame ionization detector. The quantity of trans-lactide has already fallen to a few percent after recrystallizing once from ethyl acetate, e.g. in the ratio of 1 g lactide/ml of ethyl-acetate.

3. Extraction

A solution of 31.3 g of the unpurified lactide in 100 ml of dichloromethane was shaken for 1 minute at 22° C. with a solution of 40 g of sodium chloride in 150 ml of water. A solution of 4.74 g of sodium hydrogen carbonate in 70 ml of water was then added (the ratio of the number of meq of base and base consumption per kg of lactide, hereinafter to be termed f, is 4.7) and the mixture was shaken for a further 2 minutes. The dichloromethane layer was separated off and filtered through filter paper. The dichloromethane was then distilled off under reduced pressure, finally approximately 5 mbar, the temperature of the mixture not rising above approximately 25° C. The residue weighed 26.8 g. Sublimation at a pressure of approximately 5 mbar produced from this residue 23.8 g of purified lactide (76% of the starting weight). In a check titration of the lactide thus purified, a base consumption of only 3.2 meq per kg of lactide was found.

4. Polymerization

After adding a 5% solution of 4.0 mg stannous octanoate in toluene, 20 g of the lactide so obtained was heated at 160° C. in a glass tube, sealed at approximately 1 mbar, for 17 hours in a furnace with forced air circulation, the mixture being stirred for the first 20 minutes by slowly rotating the tube about an axis perpendicular to the longitudinal axis. The relative viscosity of the polymer so obtained [i.e., the ratio of the outflow times of a solution of the polymer, in chloroform, concentration 0.500 g per 100 ml, and of chloroform alone, both at a temperature of 30.0° C.] was 1.78. To determine the outflow times, a KPG Ubbelohde viscometer with Oc capillary, diameter 0.46 mm was used.

5. Copolymerization

A mixture of 12.06 g of the same lactide and 7.94 g of glycolide (molar ratio 55/45) was polymerized in the same manner as described under 4.; the relative viscosity of the copolymer obtained was 1.66.

EXAMPLE 2

3.31 g of the unpurified lactide from Example 1 was extracted in the manner described in 1.3., but with a solution of 180 mg of sodium carbonate (f=2.7) instead of sodium hydrogen carbonate. The residue, 2.91 g (88% of the initial weight), had a base consumption of only 3.0 meq per kg of lactide after sublimation.

In another similar test, starting from 3.33 g of lactide and 180 mg of sodium carbonate, 2.97 g of residue (89%) was obtained, with a base consumption after sublimation of 3.4 meq per kg.

EXAMPLE 3

The unpurified lactide from Example 1 (3.32 g) was extracted in the manner described thereunder with a solution of 144 mg of sodium hydroxide (f=2.8) instead of sodium hydrogen carbonate. The evaporation residue was 2.58 g (78% of the starting weight), and the base consumption of the sublimated lactide was only 8.4 meq per kg.

EXAMPLE 4

The unpurified lactide from Example 1 was extracted in the same manner as described thereunder (f=2.9), starting, however, from a solution of 2.54 g of lactide in 10 ml of ethyl acetate instead of dichloromethane. After evaporating the ethyl acetate, the residue weighed 2.05 g (81%) and a base consumption of only 3.2 meq per kg was found for the sublimated lactide.

EXAMPLE 5

A solution of 60.96 g of unpurified lactide, obtained in the same manner as in Example 1, in 200 ml of dichloromethane was stirred with a sodium chloride solution. A solution of 11.72 g of sodium hydrogen carbonate in water (f=6.0) was then added while stirring in ½ minute and finally, stirring was continued for a further 2 minutes.

The dichloromethane was distilled off while carefully heating at a pressure of approximately 0.85 bar. Distillation at a pressure of approximately 5 mbar then produced 31.27 g of lactide (51.3% of the initial weight), for which a base consumption of only 5.7 meq per kg of lactide was found.

EXAMPLE 6

293.2 g of unpurified lactide was obtained from 500.2 g of 90% L-lactic acid and 2.50 g of zinc powder in the same manner as in Example 1; the base consumption was 548 meq per kg of lactide. In gas chromatographic analysis, a ratio of 7.4% trans- and 92.6% cis-lactide was found.

Extraction. A solution of 3.00 g of the unpurified lactide in dichloromethane was extracted with a solution of 405 mg of sodium hydrogen carbonate in water (f=2.9) in the manner described in Example 1. The residue was 2.46 g, 82% of the initial weight. After sublimation, 2.32 g of lactide (77%) were obtained and the base consumption had dropped to 3.0 meq per kg of lactide.

EXAMPLE 7

A solution of 60.00 g of unpurified lactide, obtained as described in Example 6, in dichloromethane was extracted with a solution of 8.09 g of sodium hydrogen carbonate (f=2.9). The product was distilled at a pressure of approximately 5 mbar, and the boiling point was approximately 115° C. The distillate weighed 45.79 g, 76.3% of the initial weight. The base consumption had dropped to the very low value of 2.3 meq per kg. In gas chromatographic analysis, a ratio of 8.5% trans- to 91.5% cis-lactide was found.

Polymerization. The purified lactide was polymerized for 17 hours at 160° C. in the manner described in Example 1.4; the relative viscosity of the polymer was 2.87. In a second experiment the purified lactide was polymerized for 6 hours at 190° C.; the relative viscosity of the final product was now lower, namely 1.62.

I claim:

1. Method for preparing polylactic acid or copolymers of lactic acid by polymerizing the lactide according to formula I:

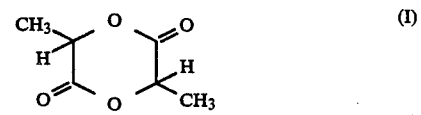

comprising forming the lactide according to formula I by polycondensation of L-, D- or D, L-lactic acid followed by decomposition of the low-molecular polylactic acid thus obtained to yield crude lactide I, dissolving the crude lactide I in a liquid organic solvent that is not miscible with water, extracting the solution thus formed with a water solution comprising a basic substance that is sparingly soluble or insoluble in the organic solvent, isolating the lactide I from the organic solvent layer and polymerizing the isolated lactide I to the high-molecular polylactic acid or copolymer thereof.

2. Method for preparing the lactide formula I:

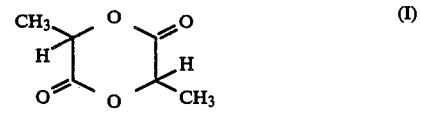

comprising the polycondensation of L-, D- or D,L-lactic acid followed by decomposition of the low-molecular polylactic acid thus obtained to yield crude lactide I, dissolving the crude lactide I obtained in an organic solvent that is not miscible with water, extracting the solution thus formed with a water solution comprising a basic substance that is sparingly soluble or insoluble in the organic solvent, and isolating the lactide from the organic solvent layer.

3. Method according to claim 1, wherein the extraction is carried out with water in which a quantity of the basic substance is dissolved which corresponds to approximately 2 to approximately 6 times the quantity of base, expressed in equivalents, which is necessary to titrate an equal quantity of crude lactide with sodium isopropanolate.

4. Method according to claim 1, wherein the organic solvent is selected from the group consisting of dichloromethane and ethyl acetate.

5. Method according to claim 1, wherein the aqueous phase comprises a high concentration of a dissolved inert salt.

6. Method according to claim 5, characterized in that sodium chloride or sodium sulphate is used as the inert salt.

7. Method according to claim 2, wherein the extraction is carried out with water in which a quantity of the basic substance is dissolved which corresponds to approximately 2 to approximately 6 times the quantity of base, expressed in equivalents, which is necessary to titrate an equal quantity of crude lactide with sodium isopropanolate.

8. Method according to claim 2, wherein the organic solvent is selected from the group consisting of dichloromethane and ethyl acetate.

9. Method according to claim 2, wherein the aqueous phase comprises a high concentration of a dissolved inert salt.

10. Method according to claim 9, characterized in that sodium chloride or sodium sulphate is used as the inert salt.

* * * * *